(12) United States Patent
Madera et al.

(10) Patent No.: US 7,247,651 B2
(45) Date of Patent: Jul. 24, 2007

(54) 2,7-SUBSTITUTED INDOLES

(75) Inventors: Ann Marie Madera, Dublin, CA (US);
Robert James Weikert, Boulder Creek, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 383 days.

(21) Appl. No.: 10/663,314

(22) Filed: Sep. 16, 2003

(65) Prior Publication Data

US 2004/0063724 A1    Apr. 1, 2004

Related U.S. Application Data

(60) Provisional application No. 60/411,239, filed on Sep. 17, 2002.

(51) Int. Cl.
*A01N 43/38* (2006.01)
*A61K 31/405* (2006.01)

(52) U.S. Cl. .................. 514/415; 548/469; 548/400; 548/416; 548/452; 548/485

(58) Field of Classification Search .............. 514/415; 548/469, 400, 416, 452, 485
See application file for complete search history.

(56) References Cited

U.S. PATENT DOCUMENTS 6,114,532 A    9/2000 Ries

2004/0024210 A1    2/2004 Johanssen et al.

FOREIGN PATENT DOCUMENTS

| EP | 1 055 668 A1 | 11/2000 |
|---|---|---|
| WO | WO 96/03400 A1 | 2/1996 |
| WO | WO 00/00198 | * 1/2000 |
| WO | WO 00/00198 A1 | 1/2000 |
| WO | WO 02/098857 | * 12/2002 |
| WO | WO 02/098857 A1 | 12/2002 |
| WO | WO 03/013510 A1 | 2/2003 |

* cited by examiner

*Primary Examiner*—James O. Wilson
*Assistant Examiner*—Paul V. Ward
(74) *Attorney, Agent, or Firm*—Robert C. Hall

(57) ABSTRACT

The present invention provides a compound of the formula:

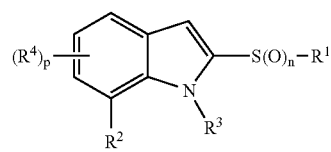

a pharmaceutically acceptable salt or a prodrug thereof, where $R^1$, $R^2$, $R^3$, $R^4$, and n are those defined herein. The present invention also provides compositions comprising, methods for using, and methods for preparing Compound of Formula I.

25 Claims, No Drawings

2,7-SUBSTITUTED INDOLES

CROSS-REFERENCE

This application claims the benefit of priority of U.S. Provisional Patent Application Ser. No. 60/411,239, filed Sep. 17, 2002, which is incorporated herein by reference in its entirety.

FIELD OF THE INVENTION

This invention relates to 2,7-substituted indoles, and associated compositions, methods for use as therapeutic agents, and methods of preparation thereof.

BACKGROUND OF THE INVENTION

The actions of the neurotransmitter 5-hydroxytryptamine (5-HT) as a major modulatory neurotransmitter in the brain, are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., *J. Pharmacol. Exp. Ther.*, 1994, 268, pages 1403–14120, D. R. Sibley et al., *Mol. Pharmacol.*, 1993, 43, 320–327, A. J. Sleight et al., *Neurotransmission*, 1995, 11, 1–5, and A. J. Sleight et al., *Serotonin ID Research Alert*, 1997, 2(3), 115–8. 5-HT6 antagonists have also been identified as potentially useful compounds for treatment of obesity. See for example, Bentley et al., *Br. J. Pharmac.* 1999, Suppl 126; Bently et al., *J. Psychopharmacol.* 1997, Suppl A64: 255; Wooley et al., *Neuropharmacology* 2001, 41: 210–129; and WO 02/098878.

While some 5-HT6 modulators have been disclosed, there continues to be a need for compounds that are useful for modulating 5-HT6.

SUMMARY OF THE INVENTION

The present invention provides a compound of the formula:

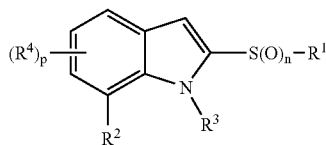

I a pharmaceutically acceptable salt or a prodrug thereof, wherein n is 0, 1 or 2;

p is 1 or 2;

$R^1$ is aryl or heteroaryl;

$R_2$ is heterocyclyl;

$R^3$ is hydrogen, alkyl, or —C(=O)—$R^5$, where $R^5$ is alkyl, alkoxy, aryl, or aryloxy; and each $R^4$ is independently hydrogen, hydroxy, cyano, alkyl, alkoxy, thioalkyl, alkylthio, halo, haloalkyl, hydroxyalkyl, nitro, alkoxycarbonyl, alkylcarbonyl, alkylsulfonyl, arylsulfonyl, haloalkylsulfonyl, amino, alkylamino, dialkylamino, alkyl(aryl)amino, alkylaminocarbonyl, alkylcarbonylamino, alkylcarbonyl(alkylamino), alkylaminosulfonyl, alkylsulfonylamino or methylenedioxy.

The present invention also provides methods for preparing, compositions comprising, and methods for using Compounds of Formula I.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve, preferably one to four, carbon atoms. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkoxy" refers to a moiety of the formula —$OR^a$ where $R^a$ is alkyl as defined herein.

"Antagonist" refers to a compound that diminishes or prevents the action of another compound or receptor site.

"Aryl" means a monovalent cyclic aromatic hydrocarbon moiety consisting of a mono- or bicyclic aromatic ring. The aryl group can optionally be substituted with one, two or three, preferably one or two, substituents, wherein each substituent is independently hydroxy, cyano, alkyl, alkoxy, thioalkyl, halo, haloalkyl, hydroxyalkyl, nitro, alkoxycarbonyl, alkylcarbonyl, alkylsulfonyl, arylsulfonyl, haloalkylsulfonyl, amino, alkylamino, dialkylamino, alkyl(aryl)amino, alkylaminocarbonyl, alkylcarbonylamino, alkylcarbonyl(alkylamino), alkylaminosulfonyl, alkylsulfonylamino or methylenedioxy, unless otherwise specifically indicated. Preferred substituents are alkyl, alkoxy, halo, or haloalkyl. Examples of aryl moieties include, but are not limited to, optionally substituted phenyl and optionally substituted naphthyl, and the like.

"Aryloxy" refers to a moiety of the formula —$OR^b$ where $R^b$ is aryl as defined herein.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like.

"Disease state" means any disease, condition, symptom, or indication.

The terms "halo," "halide," and "halogen" are used interchangeably herein and refer to a substituent fluoro, chloro, bromo, or iodo, preferably fluoro or bromo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Heteroaryl" means a monovalent mono-, bi-, or tri-cyclic aromatic moiety of 5 to 12 ring atoms containing one, two, three, or four ring heteroatoms selected from N, O, or S, the remaining ring atoms being C. The heteroaryl ring is optionally substituted independently with one or more substituents, preferably one or two substituents, selected from hydroxy, cyano, alkyl, alkoxy, thioalkyl, alkylthio, halo, haloalkyl, hydroxyalkyl, nitro, alkoxycarbonyl, alkylcarbonyl, alkylsulfonyl, arylsulfonyl, haloalkylsulfonyl, amino, alkylamino, dialkylamino, alkyl(aryl)amino, alkylaminocarbonyl, alkylcarbonylamino, alkylcarbonyl(alkylamino), alkylaminosulfonyl, alkylsulfonylamino or methylenedioxy, unless otherwise specifically indicated. Preferred substituents are alkyl, alkoxy, haloalkyl, or halo. More specifically the term heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like.

"Heterocyclyl" means a monovalent saturated moiety, consisting of one to three rings, incorporating one, two, or three heteroatoms (chosen from nitrogen, oxygen or sulfur). Examples of heterocyclyl moieties include, but are not limited to, morpholino, piperazinyl, piperidinyl, pyrrolidinyl, tetrahydropyranyl, azitidinyl, and the like.

"Leaving group" means the group with the meaning conventionally associated with it in synthetic organic chemistry, i.e., an atom or group displaceable under substitution reaction conditions. It should be appreciated that a particular leaving group depends on the reaction conditions including the atom to which the leaving group is attached to. For example, leaving groups for sulfonyl compounds include, but are not limited to, halogen, sulfonates, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:
  acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trifluoroacetic acid, trimethylacetic acid, and the like; or
  salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulfuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Prodrug" or "pro-drug" means a pharmacologically inactive form of a compound which must be metabolized in vivo, e.g., by biological fluids or enzymes, by a subject after administration into a pharmacologically active form of the compound in order to produce the desired pharmacological effect. The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Similarly, the term "hydroxy protecting group" refers to those organic groups intended to protect the oxygen atom of a hydroxyl group against undesirable reactions during synthetic procedures. Exemplary hydroxy protecting groups include, but are not limited to benzyl, silyl groups, tetrahydropyranyl, esters, and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature.

Compounds of the Present Invention

In one aspect, the present invention provides a compound of the formula:

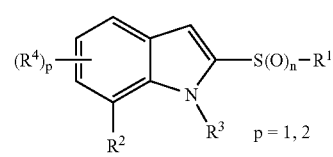

I a pharmaceutically acceptable salt or a prodrug thereof, wherein n is 0, 1 or 2; preferably n is 2;

p is 1 or 2, preferably p is 1;

$R^1$ is aryl or heteroaryl;

$R^2$ is heterocyclyl;

$R^3$ is hydrogen, alkyl, or —C(=O)—$R^5$, where $R^5$ is alkyl, alkoxy, aryl, or aryloxy; and each $R^4$ is independently hydrogen, hydroxy, cyano, alkyl, alkoxy, thioalkyl, alkylthio, halo, haloalkyl, hydroxyalkyl, nitro, alkoxycarbonyl, alkylcarbonyl, alkylsulfonyl, arylsulfonyl, haloalkylsulfonyl, amino, alkylamino, dialkylamino, alkyl(aryl)amino, alkylaminocarbonyl, alkylcarbonylamino, alkylcarbonyl(alkylamino), alkylaminosulfonyl, alkylsulfonylamino or methylenedioxy; preferably $R^4$ is hydrogen, alkyl, alkoxy, halo, or haloalkyl.

It is to be understood that the scope of this invention encompasses not only the various isomers which may exist but also the various mixture of isomers which may be formed. Furthermore, the scope of the present invention also encompasses solvates and salts of Compounds of Formula I.

Preferably, $R^1$ is thienyl or phenyl which is optionally substituted with one or more substituents selected from the group consisting of alkyl, alkoxy, halo, haloalkyl, —$SO_2$—$R^a$, —$NR^aR^b$, —$NR^b$—C(=O)—$R^a$, where $R^a$ is alkyl or aryl, and $R^b$ is hydrogen or alkyl, and a mixture thereof. More preferably, $R^1$ is thien-2-yl, phenyl, 2,3-dichlorophenyl, 2-fluorophenyl, 2-methylphenyl, 2-trifluoromethylphenyl, or 3-bromophenyl.

Preferably, $R^2$ is optionally substituted piperazinyl or piperidinyl. More preferably, $R^2$ is optionally substituted piperazin-1-yl or piperidin-4-yl. Still more preferably, $R^2$ is piperazin-1-yl, 4-methylpiperazin-1-yl, 3,5-dimethylpiperazin-1-yl, N-methyl piperidin-4-yl or piperidin-4-yl. In one particular embodiment, $R^2$ is 4-methylpiperazin-1-yl.

Preferably, $R^3$ is hydrogen or methyl.

Preferably, $R^4$ is hydrogen.

Still further, combinations of the preferred groups described herein will form other preferred embodiments. For example, in one particularly preferred embodiment $R^1$ is phenyl, n is 2, $R^2$ is piperazin-1-yl, $R^3$ is hydrogen or methyl, and $R^4$ is hydrogen. In this manner, a variety of preferred compounds are embodied within the present invention.

Some of the representative Compounds of Formula I are shown in Table 1 below:

TABLE 1

Representative Compounds of Formula I:

| Cpd. No. | Structure | Name | pKi | M + H | Example |
|---|---|---|---|---|---|
| 1 | 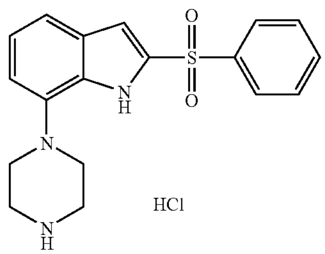 | 2-Benzenesulfonyl-7-piperazin-1-yl-1H-indole | 9.3 | 342 | 1 |
| 2 | 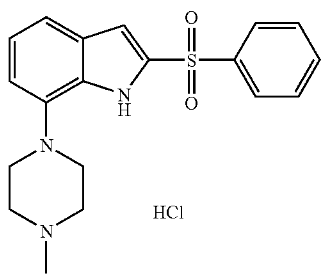 | 2-Benzenesulfonyl-7-(4-methyl-piperazin-1-yl)-1H-indole | 9.1 | 356 | 2 |
| 3 | 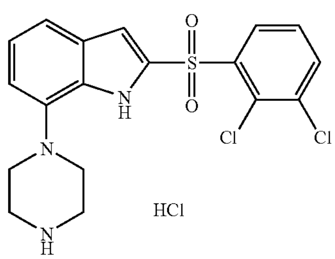 | 2-(2,3-Dichloro-benzenesulfonyl)-7-piperazin-1-yl-1H-indole | 9.7 | 410 | 1 |
| 4 | 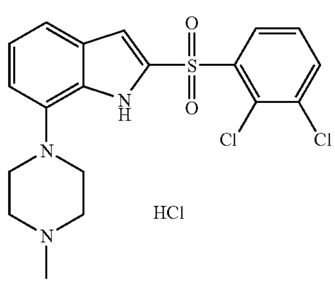 | 2-(2,3-Dichloro-benzenesulfonyl)-7-(4-methyl-piperazin-1-yl)-1H-indole | 9.1 | 424 | 2 |
| 5 | 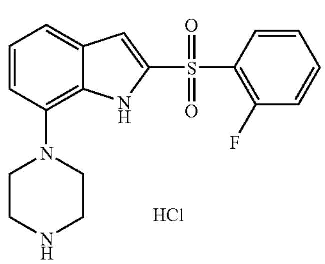 | 2-(2-Fluoro-benzenesulfonyl)-7-piperazin-1-yl-1H-indole | 9.3 | 360 | 1 |

TABLE 1-continued

Representative Compounds of Formula I:

| Cpd. No. | Structure | Name | pKi | M + H | Example |
|---|---|---|---|---|---|
| 6 | 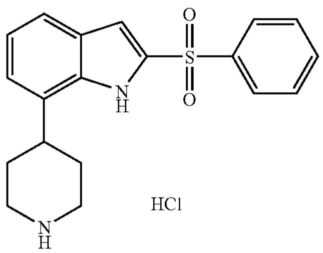 | 2-Benzenesulfonyl-7-piperidin-4-yl-1H-indole | 9.2 | 339 | 3 |
| 7 | 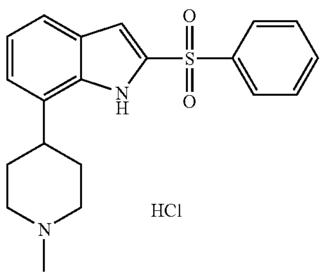 | 2-Benzenesulfonyl-7-(1-methyl-piperidin-4-yl)-1H-indole | 9 | 355 | 5 |
| 8 | 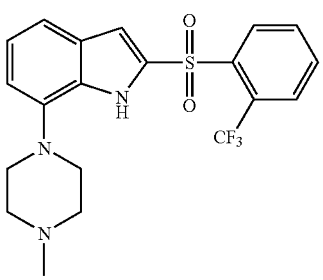 | 7-(4-Methyl-piperazin-1-yl)-2-(2-trifluoromethyl-benzenesulfonyl)-1H-indole | 9.5 | | 4 |
| 9 | 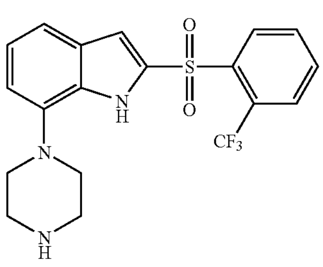 | 7-Piperazin-1-yl-2-(2-trifluoromethyl-benzenesulfonyl)1H-indole | 9.5 | | 3 |
| 10 | 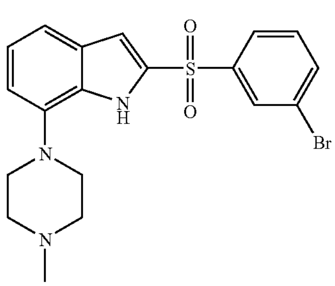 | 2-(3-Bromo-benzenesulfonyl)-7-(4-methyl-piperazin-1-yl)-1H-indole | 9.6 | | 4 |

TABLE 1-continued

Representative Compounds of Formula I:

| Cpd. No. | Structure | Name | pKi | M + H | Example |
|---|---|---|---|---|---|
| 11 | 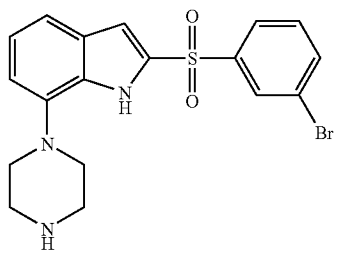 | 2-(3-Bromo-benzenesulfonyl)-7-piperazin-1-yl-1H-indole | 9.3 | | 3 |

Another aspect of the present invention provides a composition comprising a therapeutically effective amount of a Compound of Formula I and a pharmaceutically acceptable carrier.

Yet another aspect of the present invention provides a method for treating a CNS disease state in a subject comprising administering to the subject a therapeutically effective amount of a Compound of Formula I. Preferably, the disease state comprises psychoses, schizophrenia, manic depressions, neurological disorders, memory disorders, attention deficit disorder, Parkinson's disease, amyotrophic lateral sclerosis, Alzheimer's disease and Huntington's disease.

Still another aspect of the present invention provides a method for treating a disorder of the gastrointestinal tract in a subject comprising administering to the subject a therapeutically effective amount of a Compound of Formula I.

Another aspect of the present invention provides a method for producing a Compound of Formula I.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis;* Wiley & Sons: New York, 1991, Volumes 1–15; *Rodd's Chemistry of Carbon Compounds,* Elsevier Science Publishers, 1989, Volumes 1–5 and Supplementals; and *Organic Reactions,* Wiley & Sons: New York, 1991, Volumes 1–40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

In one embodiment, Compounds of Formula I, are prepared by deprotonating a substituted indole of the formula:

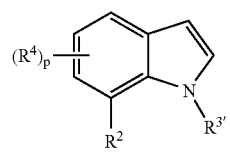

II with a base and adding a sulfonylating agent of the formula: Y—SO$_2$—R$^1$, where R$^1$, R$^2$, and R$^4$ are those defined herein, R$^{3'}$ is alkyl or —C(=O)—R$^5$, where R$^5$ is that defined herein, and Y is a leaving group, preferably halide, and more preferably fluoride. It should be appreciated that when R$^2$ and/or R$^4$ has one or more acidic protons (relative to the base used), it should be protected with an appropriate protecting group. Suitable protecting groups for such acidic protons are well known to one skilled in the art and depends on the nature of the acidic proton, e.g., whether it is an amino proton or hydroxy proton, etc.

The base should be strong enough to deprotonate primarily the 2-position of the indole ring system. Such bases are well known to one skilled in the art and include organometallic compounds such as organolithiums, for example, tert-butyllithium, and Grignard reagents, for example, tert-butylmagnesium halide. Generally, the deprotonation reaction is conducted at a temperature of about 0° C. or below, preferably about −40° C. or below, and more preferably about −70° C. or below. Typically, the deprotonation reaction is conducted at about −75° C.

Suitable sulfonylating agent include arylsulfonylhalides, for example, arylsulfonylfluorides. Arylsulfonylfluorides can be readily prepared from the corresponding arylsulfonylchlorides by treatment with a fluoride source, such as potassium fluoride or other suitable metallic fluoride compounds. Conversion of the arylsulfonylchloride to its corresponding fluoride derivative typically involves reacting the arylsulfonylchloride with potassium fluoride in an inert organic solvent, such as 1,4-dioxane. The reaction is generally carried out under refluxing conditions for a period of about 1 to about 48 hours, typically about 24 hours. Generally, excess potassium fluoride is used in the reaction, which can be readily removed during a work-up process by washing with water. The resulting arylsulfonylfluoride is typically used without any further purification.

Alternatively, Compounds of Formula I can also be prepared by reacting the deprotonated indole group with a disulfide reagent of the formula: $R^1$—S—S—$R^1$ to produce a thioether of the formula:

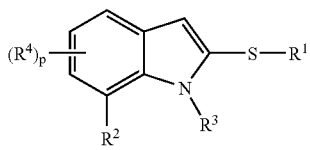

III where p, $R^1$, $R^2$, $R^{3'}$, and $R^4$ are those defined herein. Typically, the disulfide reagent is added to the deprotonated indole at the same temperature in which the base is added. The reaction mixture is then stirred at that temperature for few minutes to few hours, typically from about 1 to 2 hours, and is allowed to gradually warm to room temperature.

The thioether compound of Formula III can be oxidized using an oxidizing agent to produce a corresponding sulfoxide and/or sulfone. Suitable oxidizing agents include meta-chloroperbenzoic acid (MCPBA), periodates, Oxone®, as well as other sulfur oxidizing agents known to one skilled in the art. For example, the thioether III can be reacted with MCPBA by combining the two reagents at about 0° C. in an inert solvent, such as dichloromethane, and stirring the mixture at room temperature for few hours. The excess MCPBA is typically removed by washing with an aqueous, preferably a basic aqueous, solution. Any undesired oxidation of nitrogen atom can be reduced by quenching the crude product with a phosphine compound, such as triphenylphosphine.

When $R^1$ or $R^2$ group contains a protecting group, or when $R^{3'}$ is a protecting group, such protecting group can be removed after the synthesis using reaction conditions conventionally known to one skilled in the art. See, for example, *Protective Groups in Organic Synthesis*, $3^{rd}$ edition, T. W. Greene and P. G. M. Wuts, John Wiley & Sons, New York, 1999, which is incorporated herein by reference in its entirety.

More specific details for producing Compounds of Formula I are described in the Examples section.

Utility

The compounds of the invention have selective 5-HT6 receptor affinity and are useful in the treatment of certain CNS disorders, such as Parkinson's disease, Huntington's disease, anxiety, depression, manic depression, psychosis, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. In addition, compounds of the present invention are also useful in the treatment of certain GI (gastrointestinal) disorders, such functional bowel disorder.

Testing

The pharmacology of the compounds of this invention was determined by art recognized procedures. The in vitro techniques for determining the affinities of test compounds at the 5-HT6 receptor in radioligand binding and functional assays are described in Examples 6-8.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 6–12.

EXAMPLES

The following preparations and examples are given to enable those skilled in the art to more clearly understand and to practice the present invention. They should not be considered as limiting the scope of the invention, but merely as being illustrative and representative thereof.

Example 1

This example illustrates a method for producing Compounds of Formula I using the synthetic scheme outlined below:

Preparation of 2-benzenesulfonyl-7-piperazin-1-yl-1H-indole

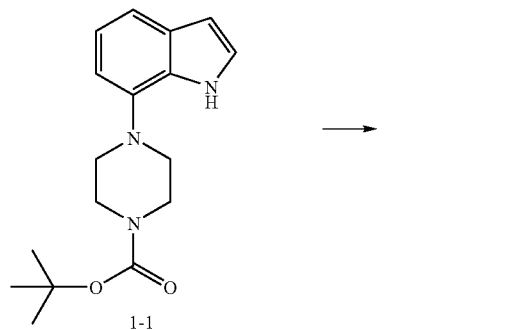

1-1

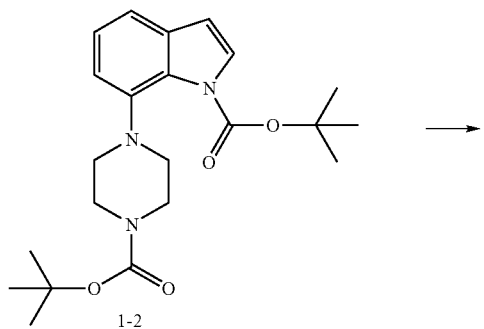

1-2

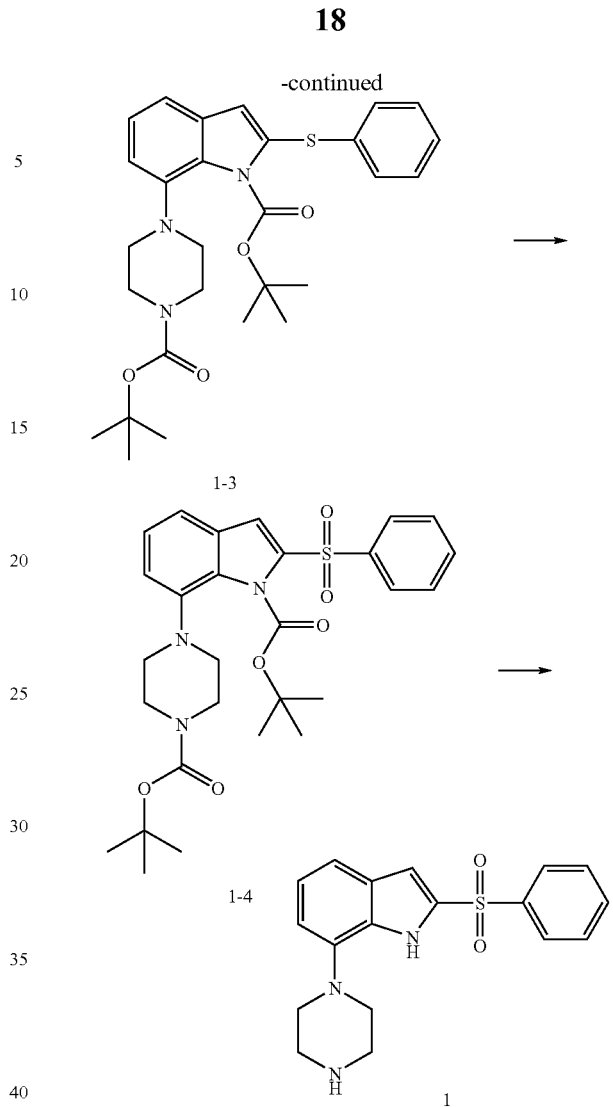

Step 1

To a solution of 4-(1H-indol-7-yl)-piperazine-1-carboxylic acid tert-butyl ester 1-1 (1.22 g, 4.0 mmol) in THF (40 mL) at room temperature was added di-tert-butyl dicarbonate (1.3 g, 6.1 mmol) followed by DMAP (56 mg, 0.46 mmol). The reaction mixture was stirred at room temperature under nitrogen for 3 hours then concentrated in vacuo. The remaining residue was partitioned between ethyl acetate (50 mL) and a saturated aqueous sodium bicarbonate solution (50 mL). The organic layer was washed with a saturated aqueous sodium bicarbonate solution (2×25 mL), then with brine (25 mL). The organic layer was dried (MgSO$_4$), filtered, and concentrated to afford a clear oil. The oil was chromatographed on silica gel eluting with hexanes/ethyl acetate (23:1) to afford 1.5 g (93%) of 7-(4-tert-butoxycarbonyl-piperazin-1-yl)-indole-1-carboxylic acid tert-butyl ester 1-2 as a white solid. (M+H)$^+$=402.2.

Step 2

To a −75° C. solution of the 7-(4-tert-butoxycarbonyl-piperazin-1-yl)-indole-1-carboxylic acid tert-butyl ester 1-2 (500 mg, 1.25 mmol) in THF (25 mL) under inert atmosphere was slowly added t-BuLi (1.47 mL, 2.5 mmol). The reaction mixture was stirred for 30 minutes at which time diphenyldisulfide (340 mg, 1.63 mmol) was added. The reaction was stirred for 1.5 h then allowed to warm to room temperature (45 min). The reaction mixture was quenched with a saturated solution of ammonium chloride (55 mL), and extracted with ethyl acetate (3×20 mL). The combined ethyl acetate layers were washed with brine (25 mL), dried (MgSO$_4$), filtered, and concentrated to afford a yellow oil. The oil was chromatographed over silica gel eluting with hexanes/ethyl acetate (23:1) to afford 440 mg (69%) of 7-(4-tert-butoxycarbonyl-piperazin-1-yl)-2-phenylsulfanyl-indole-1-carboxylic acid tert-butyl ester 1-3.

Steps 3 and 4

To a solution of 7-(4-tert-butoxycarbonyl-piperazin-1-yl)-2-phenylsulfanyl-indole-1-carboxylic acid tert-butyl ester 1-3 (440 mg, 0.86 mmol) in dichloromethane (40 mL) at 0° C. was added MCPBA (745 mg, 3.02 mmol). The reaction was warmed to room temperature and stirred for 5 h, at which time triphenylphosphine (271 mg, 1.03 mmol) was added. The reaction mixture was stirred at room temperature overnight. The reaction mixture was partitioned between water (50 mL) and dichloromethane (50 mL). The organic layer was washed with 1 M sodium hydroxide (3×35 mL) and brine (35 mL). The organic layer was dried (MgSO$_4$), filtered and concentrated. The remaining oil was chromatographed over silica gel eluting with hexanes/ethyl acetate (17:3) to afford 160 mg (34%) of 2-benzenesulfonyl-7-(4-tert-butoxycarbonyl-piperazin-1-yl)-indole-1-carboxylic acid tert butyl ester 1-4. M+H=542.

Step 5

A solution of 2-benzenesulfonyl-7-(4-tert-butoxycarbonyl-piperazin-1-yl)-indole-1-carboxylic acid tert butyl ester 1-4 (160 mg, 0.3 mmol) in isopropanol (15 mL) and concentrated HCl (4 mL) was refluxed for 1 hour. The reaction mixture was concentrated and the remaining powder was triturated with isopropanol (10 mL) and ether (20 mL). This was filtered to afford 2-benzenesulfonyl-7-piperazin-1-yl-1H-indole, Compound 1 of Table 1 as a white solid (90 mg, 89%). M+H=342.

Example 2

This example illustrates a method for preparing Compound 2 of Table 1.

2-benzenesulfonyl-7-(4-methyl-piperazin-1-yl)-1H-indole

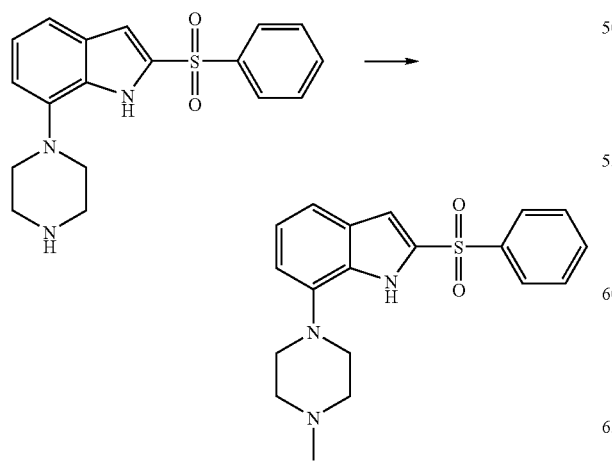

To a solution of 2-benzenesulfonyl-7-piperazin-1-yl-1H-indole, Compound 1 of Table 1 (see Example 1 above) (340 mg, 1.04 mmol) in THF (50 mL) was added formaldehyde (37%, 0.4 mL, 5.2 mmol) followed by sodium triacetoxyborohydride (330 mg, 1.56 mmol). The reaction mixture was stirred at room temperature for 24 hrs. The mixture was partitioned between ethyl acetate (50 mL) and water (50 mL). The acetate layer was washed with brine, dried (MgSO$_4$) and concentrated to afford a white solid. The solid was dissolved in ether (30 mL) and treated with excess 1 M HCl in ether. The white precipitate was collected and dried to afford pure product 2-benzenesulfonyl-7-piperazin-1-yl-1H-indole (Compound 2 of Table 1).

Example 3

This example illustrates a method for preparing Compound 6 of Table 1, 2-benzenesulfonyl-7-piperidin-4-yl-1H-indole.

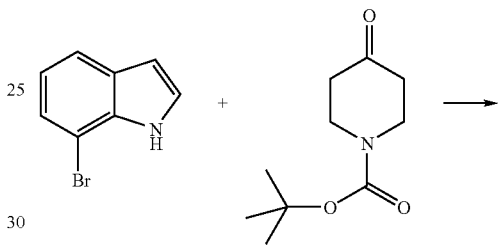

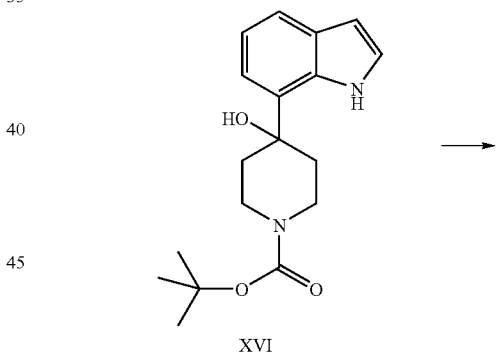

XVI

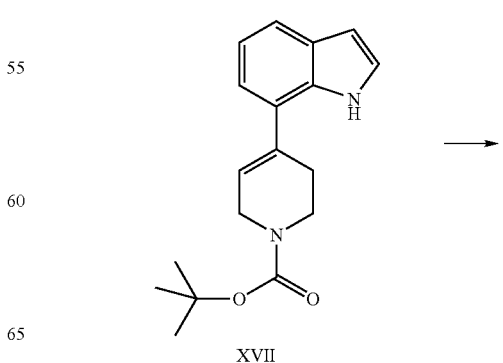

XVII

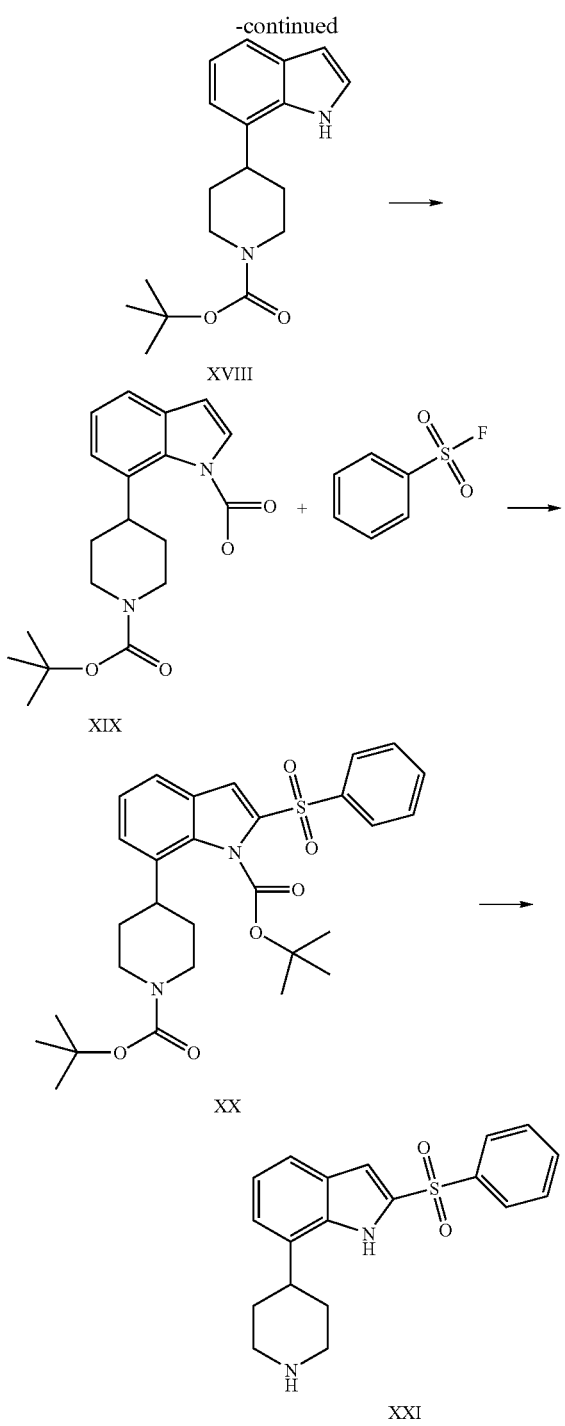

acetate (50 mL). The organic layer was washed with water (15 mL) and brine (30 mL), then dried (MgSO$_4$), filtered and concentrated. The remaining brown oil was chromatographed, eluting with acetone:hexanes (1:4) to afford 1.17 g (58% yield) of 4-hydroxy-4-(1-H-indol-7-yl)-piperidine-1-carboxylic acid tert-butyl ester XVI.

Step 2

4-Hydroxy-4-(1-H-indol-7-yl)-piperidine-1-carboxylic acid tert-butyl ester XVI (1.17 g, 3.7 mmol) was combined with pyridine (20 mL) and phosphorus oxychloride (0.7 mL, 7.4 mmol) at room temperature under nitrogen, and was stirred overnight. The reaction was partitioned between ethyl acetate (55 mL) and water (55 mL). The ethyl acetate layer was washed with water (2×30 mL) and brine (55 mL), then dried (MgSO$_4$), filtered and concentrated to afford (700 mg, 64%) of 4-(1H-indol-7-yl)-3,6-dihydro-2H-pyridine-1-carboxylic acid tert-butyl ester XVII.

Step 3

A mixture of 4-(1H-indol-7-yl)-3,6-dihydro-2H-pyridine-1-carboxylic acid tert-butyl ester XVII (700 mg, 2.3 mmol) and 10% Pd/C (70 mg) in ethanol (75 mL) was placed under H$_2$ atmosphere on the parr shaker at 50 psi, and was shaken overnight. The reaction mixture was filtered through a plug of celite capped with a glass filter. The filtrate was concentrated to afford (680 mg, 95%) of 4-(1H-indol-7-yl)-piperidine-1-carboxylic acid tert-butyl ester XVIII.

Step 4

To a solution of 4-(1H-indol-7-yl)-piperidine-1-carboxylic acid tert-butyl ester XVIII (360 mg, 1.2 mmol) in THF (30 mL) at room temperature was added di-tert-butyl dicarbonate (262 mg, 1.2 mmol) followed by a catalytic amount of DMAP (5.6 mg, 0.046 mmol). The reaction mixture was allowed to stir at room temperature under nitrogen for 24 hours at which time the reaction mixture was stripped. The remaining residue was partitioned between ethyl acetate (50 mL) and saturated sodium bicarbonate (50 mL). The organic layer was washed with saturated sodium bicarbonate (2×25 mL), and with brine (25 mL). The organic layer was dried (MgSO$_4$), filtered, and concentrated to afford a clear oil. The oil was chromatographed eluting with hexanes/ethyl acetate (23:1) to afford 400 mg (83%) of 7-(1-tert-butoxycarbonyl-piperazin-4-yl)-indole-1-carboxylic acid tert-butyl ester XIX.

Step 5

To a −75° C. solution of 7-(1-tert-butoxycarbonyl-piperidin-4-yl)-indole-1-carboxylic acid tert-butyl ester XIX (440 mg, 1.0 mmol) in THF (20 mL) was slowly added t-BuLi (1.2 mL, 2.0 mmol). The reaction mixture was stirred for 45 minutes at −75° C., and the benzenesulfonyl fluoride (0.2 mL, 1.6 mmol, see Example 4 below) was added. The reaction was stirred for 2.5 h at which time the cold bath was removed and the reaction was allowed to warm to room temperature. The reaction was quenched with a saturated solution of ammonium chloride (25 mL) and extracted with ethyl acetate (3×20 mL). The combined ethyl acetate layers were washed with brine (25 mL), dried (MgSO$_4$), filtered and stripped to afford a yellow oil. The oil was chromatographed over silica eluting with hexanes/ethyl acetate (4:1) to afford (330 mg, 60%) of the product 2-benzenesulfonyl-7-(1-tert-butoxycarbonyl-piperidin-4-yl)-indole-1-carboxylic acid tert-butyl ester XX.

Step 6

2-Benzenesulfonyl-7-(1-tert-butoxycarbonyl-piperidin-4-yl)-indole-1-carboxylic acid tert-butyl ester XX (330 mg, Step 1

A solution of 7-bromoindole (1.25 g, 6.4 mmol) in THF (15 mL) under Argon was cooled to −70° C., and n-BuLi (9.6 mL, 19.2 mmol) was added over 20 min. The reaction mixture was warmed to −5° C. in an ice bath and was stirred at this temperature for 30 min. The mixture was cooled to −70° C. and a solution of N-Boc-piperidone (2.5 g, 12.8 mmol) in THF (10 mL) was added over 15 min. The reaction was stirred for 45 min at −70° C. and was then warmed to room temperature. The reaction was quenched with water (10 mL) and partitioned between water (25 mL) and ethyl 0.61 mmol) was dissolved in 1 M ethanolic HCl (30 mL) and warmed to reflux. After 2.5 h, the reaction mixture was cooled to room temperature and ether (30 mL) was added. The white precipitate was collected to afford 210 mg (91%) of the product 2-benzenesulfonyl-7-piperidin-4-yl)-1H-indole XXI.

Example 4

This example illustrates a method for preparing benzenesulfonyl fluoride.

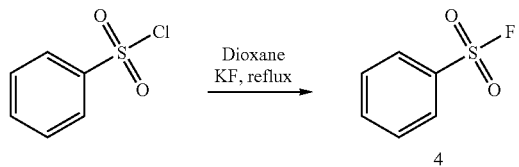

Potassium fluoride (99%) (12 g, 216 mmol) was added to a solution of benzenesulfonyl chloride (51 mmol) in 1,4 dioxane (35 mL). The reaction mixture was refluxed for 24 hrs. then cooled to room temperature and poured into ice water (200 mL). The ice water was extracted with chloroform (3×50 mL). The combined chloroform layers were dried (MgSO$_4$), filtered, and concentrated to afford benzenesulfonyl fluoride (4).

Example 5

This example illustrates a method for preparing Compound 7 of Table 1, 2-benzenesulfonyl-7-(1-methyl-piperidin-4-yl)-1H-indole

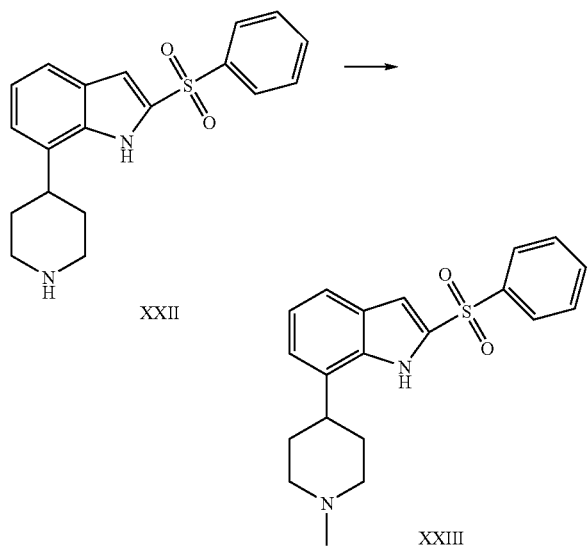

Sodium triacetoxyborohydride (110 mg, 0.52 mmol) was added in a single portion to a solution of 2-benzenesulfonyl-7-piperidin-4-yl)-1H-indole XXI (130 mg, 0.34 mmol, see Example 3 above) and formaldehyde (30%) (0.14 mL, 1.7 mmol) in THF (20 mL) under inert atmosphere. The reaction was stirred for 24 hr, then concentrated in vacuo. The residue was partitioned between 1 M sodium hydroxide (25 mL) and ethyl acetate (25 mL). The aqueous layer was extracted with ethyl acetate (2×15 mL). The combined organic layers were dried (MgSO$_4$), filtered and a solution of 1 M HCl in ether was added to the filtrate. The precipitate was collected to afford 130 mg (98%) of 2-benzenesulfonyl-7-(1-methyl-piperidin-4-yl)-1H-indole XXIII as a white powder.

Example 6

This example illustrates in vitro radioligand binding studies of Compound of Formula I.

The binding activity of compounds of this invention in vitro was determined as follows. Duplicate determinations of ligand affinity are made by competing for binding of [$^3$H]LSD in cell membranes derived from HEK293 cells stably expressing recombinant human 5-HT6 receptor.

All determinations were made in assay buffer containing 50 mM Tris-HCl, 10 mM MgSO$_4$, 0.5 mM EDTA, 1 mM ascorbic acid, pH 7.4 at 37° C., in a 250 microliter reaction volume. Assay tubes containing [3H] LSD (5 nM), competing ligand, and membrane were incubated in a shaking water bath for 60 min. at 37° C., filtered onto Packard GF-B plates (pre-soaked with 0.3% PEI) using a Packard 96 well cell harvester and washed 3 times in ice cold 50 mM Tris-HCl. Bound [$^3$H] LSD was determined as radioactive counts per minute using Packard TopCount.

Displacement of [3H]LSD from the binding sites was quantified by fitting concentration-binding data to a 4-parameter logistic equation:

$$binding = basal + \left( \frac{B\max - basal}{1 + 10^{-Hill(\log[ligand] - \log IC_{50})}} \right)$$

where Hill is the Hill slope, [ligand] is the concentration of competing radioligand and IC$_{50}$ is the concentration of radioligand producing half-maximal specific binding of radioligand. The specific binding window is the difference between the Bmax and the basal parameters.

Example 7

Using the procedures of Example 6, compounds of Formula I were tested and found to be selective 5-HT6 antagonists. Representative activities are shown in Table 1.

Example 8

The cognition-enhancing properties of compounds of the invention may be in a model of animal cognition: the object recognition task model. Four months old male Wistar rats (Charles River, The Netherlands) were used. Compounds were prepared daily and dissolved in physiological saline and tested at three doses. Administration was always given i.p. (injection volume 1 mL/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47–59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula:

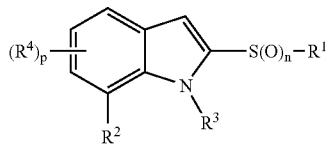

or a pharmaceutically acceptable salt thereof,
wherein
n is 0, 1 or 2;
p is 1 or 2;
$R^1$ is aryl or heteroaryl;
$R^2$ is a heterocyclyl;
$R^3$ is hydrogen, alkyl, or —C(=O)—$R^5$, where $R^5$ is alkyl, alkoxy, aryl, or aryloxy; and
each $R^4$ is independently hydrogen, hydroxy, cyano, alkyl, alkoxy, thioalkyl, alkylthio, halo, haloalkyl, hydroxyalkyl, nitro, alkoxycarbonyl, alkylcarbonyl, alkylsulfonyl, arylsulfonyl, haloalkylsulfonyl, amino, alkylamino, dialkylamino, alkyl(aryl)amino, alkylaminocarbonyl, alkylcarbonylamino, alkylcarbonyl(alkylamino), alkylaminosulfonyl, alkylsulfonylamino or methylenedioxyhydrogen, alkyl, alkoxy, halo, or haloalkyl.

2. The compound according to claim 1, wherein p is 1 and $R^4$ is located at the 6-position of the indole ring system.

3. The compound according to claim 1, wherein $R^2$ is optionally substituted piperazin-1-yl or optionally substituted piperidin-4-yl.

4. The compound according to claim 3, wherein $R^2$ is piperazin-1-yl, 4-methylpiperazin-1-yl, 3,5-dimethylpiperazin-1-yl, N-methyl piperidin-4-yl or piperidin-4-yl.

5. The compound according to claim 4, wherein $R^2$ is 4-methylpiperazin-1-yl.

6. The compound according to claim 3, wherein $R^1$ is optionally substituted phenyl.

7. The compound according to claim 6, wherein $R^1$ is phenyl which is optionally substituted with alkyl, halo or haloalkyl.

8. The compound according to claim 7, wherein $R^1$ is phenyl, 2,3-dichlorophenyl, 2-fluorophenyl, 2-methylphenyl, 2-trifluoromethylphenyl, 3-bromophenyl.

9. The compound according to claim 6, wherein n is 2.

10. The compound according to claim 9, wherein $R^3$ is hydrogen, methyl, or —C(=O)—$R^5$, where $R^5$ is alkoxy.

11. The compound according to claim 1, wherein $R^1$ is phenyl which is optionally substituted with a substituent selected from the group consisting of alkyl, halo and haloalkyl.

12. The compound according to claim 11, wherein $R^1$ is phenyl, 2,3-dichlorophenyl, 2-fluorophenyl, 2-methylphenyl, 2-trifluoromethylphenyl, or 3-bromophenyl.

13. The compound according to claim 11, wherein n is 2.

14. The compound according to claim 13, wherein $R^2$ is optionally substituted piperazin-1-yl or optionally substituted piperidin-4-yl.

15. The compound according to claim 14, wherein $R^2$ is piperazin-1-yl, 4-methylpiperazin-1-yl, 3,5-dimethylpiperazin-1-yl, N-methyl piperidin-4-yl or piperidin-4-yl.

16. The compound according to claim 15, wherein $R^3$ is hydrogen, methyl or —C(=O)—$R^5$, where $R^5$ is alkoxy.

17. The compound according to claim 1, wherein n is 2.

18. The compound according to claim 17, wherein $R^1$ is phenyl which is optionally substituted with a substituent selected from the group consisting of alkyl, halo, haloalkyl, and a mixture thereof.

19. The compound according to claim 18, wherein $R^2$ is optionally substituted piperazin-1-yl or optionally substituted piperidin-4-yl.

20. The compound according to claim 19, wherein $R^3$ is hydrogen, methyl or —C(=O)—$R^5$, where $R^5$ is alkoxy.

21. The compound according to claim 1, wherein said compound is 2-benzenesulfonyl-7-(4-methylpiperazin-1-yl)-1H-indole.

22. A method for producing a compound of claim 1, said method comprising contacting a substituted indole of the formula:

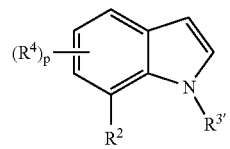

wherein $R^{3'}$ is alkyl or —C(=O)—$R^5$, and p, $R^2$, $R^4$ and $R^5$ are as recited in claim 1
(i) with a base to produce a deprotonated indole; and
(ii) contacting the deprotonated indole with a sulfonylating agent of the formula:

where Y is halide and $R^1$ is as recited in claim 1, or a disulfide agent of the formula:

to produce a 2 substituted indole of the formula:

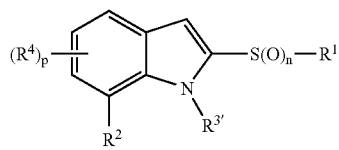

(iii) optionally oxidizing the sulfur with an oxidizing agent; and
(iv) optionally removing the group $R^{3'}$ to produce the compound of claim 1 wherein $R^3$ is hydrogen.

23. The method of claim 22, wherein Y is fluorine.

24. A composition comprising:
(a) a therapeutically effective amount of a compound of claim 1; and
(b) a pharmaceutically acceptable carrier.

25. A method for enhancing cognitive memory in Alzheimer's patients, said method comprising administering to said patient a therapeutically effective amount of a compound of claim 1.

* * * * *